United States Patent
Xue et al.

(10) Patent No.: US 11,001,823 B2
(45) Date of Patent: May 11, 2021

(54) NITRILASE MUTANTS AND APPLICATION THEREOF

(71) Applicant: ZHEJIANG UNIVERSITY OF TECHNOLOGY, Zhejiang (CN)

(72) Inventors: Yaping Xue, Zhejiang (CN); Yuguo Zheng, Zhejiang (CN); Zhe Xu, Zhejiang (CN); Zhiqiang Liu, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 16/619,344

(22) PCT Filed: Jan. 24, 2019

(86) PCT No.: PCT/CN2019/072894
§ 371 (c)(1),
(2) Date: Dec. 4, 2019

(87) PCT Pub. No.: WO2019/157921
PCT Pub. Date: Aug. 22, 2019

(65) Prior Publication Data
US 2020/0115695 A1   Apr. 16, 2020

(30) Foreign Application Priority Data
Feb. 14, 2018 (CN) .......................... 201810151771.9

(51) Int. Cl.
| | |
|---|---|
| C12N 9/78 | (2006.01) |
| C12P 13/00 | (2006.01) |
| C12N 15/00 | (2006.01) |
| C12N 1/20 | (2006.01) |
| C12N 15/63 | (2006.01) |

(52) U.S. Cl.
CPC ............... *C12N 9/78* (2013.01); *C12N 15/63* (2013.01); *C12P 13/002* (2013.01); *C12Y 305/05001* (2013.01)

(58) Field of Classification Search
CPC ....................................................... C12N 9/78
See application file for complete search history.

(56) References Cited

U.S. PATENT DOCUMENTS

| | | | | |
|---|---|---|---|---|
| 7,198,927 B2* | 4/2007 | DiCosimo | ............. | C12N 9/78 435/136 |
| 8,916,364 B2* | 12/2014 | Vogel | ............. | C12N 9/78 435/128 |

FOREIGN PATENT DOCUMENTS

| | | |
|---|---|---|
| CN | 101918573 A | 12/2010 |
| CN | 102016018 A | 4/2011 |
| CN | 102796769 A | 11/2012 |
| CN | 102796772 A | 11/2012 |
| CN | 105296512 A | 2/2016 |
| CN | 107177576 A | 9/2017 |
| CN | 108486088 A | 9/2018 |

OTHER PUBLICATIONS

Zheng. A0A0U1TDG4_9BURK. UniProtKB Dababase. 2016.*
Studer. Residue mutations and their impact on protein structure and function: detecting beneficial and pathogenic changes. Biochem. J. (2013) 449, 581-594.*
Kobayashi. NRL2_RHORH. UnitProtKB Database. 2015.*
Xue. English translation of CN107177576 via https://patents.google.com/patent/CN107177576A/en on Aug. 4, 2020.*
Robertson. Q6RWF5_9ZZZZ. UnitProtKB Database. 2015.*
International Search Report Based on Application No. PCT/CN2019/072894; dated Mar. 27, 2019.

* cited by examiner

*Primary Examiner* — Yong D Pak
(74) *Attorney, Agent, or Firm* — Muncy, Geissler, Olds & Lowe, P.C.

(57) ABSTRACT

The present invention discloses a nitrilase mutant and application thereof. The mutant is obtained by mutating the amino acid at position 201 or replacing one or more amino acids at region 324-381 of the amino acid sequence shown in SEQ ID No. 2. In the present invention, by the protein molecular modification, thermostability of the purified nitrilase LNIT5 is increased by up to 4.5 folds; and by utilizing recombinant *E. coli* containing the nitrilase mutant to hydrolyze 1-cyanocyclohexylacetonitrile at a high temperature (45° C.), product tolerance is increased, activity of NIT5-L201F is increased by 20%, and the mutant $NIT_{LNIT5\text{-}AcN}$ can completely hydrolyze 750 mM 1-cyanocyclohexylacetonitrile within 8 hours and achieve an doubled conversion rate. Therefore, the mutants obtained by the present invention have a good application prospect in efficiently catalyzing 1-cyanocyclohexylacetonitrile to synthesize gabapentin intermediate, 1-cyanocyclohexyl acetic acid. In the present invention, by protein molecular modification, thermal stability of pure nitrilase LNIT5 at 45° C. is increased up to 4.5 times, and while 1-cyanocyclohexylacetonitrile is hydrolyzed using recombinant *Escherichia coli* containing nitrilase mutant at high temperature (45° C.), the product yield is increased. Therefore, the mutants obtained in the present invention have a good application prospect in highly efficiently catalyzing 1-cyanocyclohexylacetonitrile to 1-cyanocyclohexyl acetic acid, the gabapentin intermediate.

5 Claims, 4 Drawing Sheets

Specification includes a Sequence Listing.

US 11,001,823 B2

NITRILASE MUTANTS AND APPLICATION THEREOF

TECHNICAL FIELD

The present invention relates to nitrilase mutants derived from an uncultured microorganism and their application in the synthesis of an antiepileptic drug intermediate, 1-cyanocyclohexyl acetic acid.

BACKGROUND ART

The chemical name of gabapentin is 1-aminomethyl-1-cyclohexaneacetic acid. It was developed by Warner-Lambert Company, USA, first listed in the UK in May 1993, approved by FDA and listed in the USA in 1994, and was used for epilepsy treatment in many countries around the world subsequently. In 1996, Warner-Lambert Company began to expand research on gabapentin indications, and in 2002, FDA approved its use in treatment of neuropathic pain. In addition to being used alone for treatment of general epilepsy, gabapentin is also used as a superimposed therapeutic drug for refractory epilepsy. It has advantages of good tolerance and mild side effects, is one of the drugs that are expected to promote development of the world epilepsy drug market. At present, the patent of gabapentin has expired, and countries around the world have carried out research on this product. The demand for the bulk drug is huge and the market prospect is broad.

1-Cyanocyclohexyl acetic acid is a key intermediate for synthesis of a new generation of the anti-epileptic drug, gabapentin, the market prospect is very broad. At present, all the synthesis methods of gabapentin and its key intermediate 1-cyanocyclohexyl acetic acid adopt chemical synthesis technology, and there are problems of large discharge of "three wastes", serious environmental pollution and high treatment cost of "three wastes", etc. in the production process.

Nitrilase (Nitrilase EC 3.5.5.1) is an enzyme that is able to hydrolyze nitriles (containing —CN) to the corresponding carboxylic acids. Cyano hydrolysis reaction accomplished by nitrilase has a mild reaction condition, high reaction efficiency, as well as high regioselectivity and stereoselectivity, a mild reaction condition, little environmental pollution and low cost, it is an environmentally friendly green synthesis method, meets the requirements of atom economy, and has important practical significance for energy conservation, emission reduction and building a harmonious society. Due to these excellent properties of nitrilase, it has become an extremely promising catalyst for industry. At present, there are many successful examples of nitrilase in industrial applications, the product of BASF Company, Germany, (R)-mandelic acid, firstly, racemic mandelonitrile is formed by reaction of benzaldehyde and hydrocyanic acid, and then selecting an appropriate reaction condition, through nitrilase-catalyzed dynamic kinetic resolution, it quantitatively converts to (R)-mandelic acid. DuPont Company developed an industrial process to convert 2-methylglutaronitrile (MGN, a by-product from manufacture of nylon-66 from adiponitrile) to 1,5-dimethyl-2-piperidone (1,5-DMPD). 1,5-Dimethyl-2-piperidone has satisfactory properties in electronics, coatings and solvent applications. MGN was first hydrolyzed to 4-cyanovaleric acid (4-CPA) ammonium salt by immobilized nitrilase-containing microbial cell catalyst (*Acidovorax facilis* 72W), the selectivity of the hydrolysis reaction was more than 98%, and its conversion rate was 100%, the reaction obtains one-half of ammonium cyanocarboxylate, and produces 1~2% of the only reaction by-product, 2-methylglutarate diammonium salt. Compared to a chemical process that directly converts MGN to a mixture of 1,3-DPMD and 1,5-DMPD through hydrogenation, the chemical-enzymatic process produces high yields, generates less waste, and produces a single lactam isomerization. In addition, many nitrilase enzymes have been developed and used in the synthesis of a variety of pharmaceutical intermediates and fine chemicals.

However, thermal stability of natural nitrilases is generally poor, which prevents its industrial application. The thermal stability of the enzyme can be improved by performing chemical modification or molecular modification on the enzyme. Since crystal structure of the nitrilase has been reported little, modification on the stability of nitrilases has rarely been reported.

The nitrilase cloned from *Acidovorax facilis* (*Acidovorax facilis*) CCTCC NO: 209044 has been overexpressed in *E. coli* (*Escherichia coli*) BL21 (DE3), through molecular modification it performs relatively high catalytic activity in substrate, 1-cyanocyclohexylacetonitrile, and is capable of catalyzing 1-cyanocyclohexylacetonitrile to produce the gabapentin intermediate, 1-cyanocyclohexyl acetic acid (*Catalysis Communications*, 2015, 66, 121-125). However, the biological catalyst has the problems of poor thermostability, lower catalytic efficiency at high temperature, long reaction time and the like. In subsequent studies, nitrilase derived from *Acidovorax facilis* CCTCC NO: M 209044 was modified by error-prone PCR and site-directed mutagenesis technology to increase its thermostability at 45° C. by 14 folds, which has important reference value for improving thermostability of nitrilase by utilizing the molecular modification technology.

SUMMARY OF THE INVENTION

For the problem of poor thermostability of nitrilase LNIT5 (GenBank Accession no: AAR97494.1) derived from uncultured microorganisms, the present invention provides a plurality of nitrilase mutant proteins and their application in synthesis of 1-cyanocyclohexyl acetic acid, including recombinant vectors containing the genes, and recombinant genetic engineering bacteria transformed by the recombinant vectors.

Technical solutions adopted in the present invention are as follows:

The present invention provides a nitrilase mutant, which is obtained by mutating the amino acid at position 201 or replacing amino acids at positions 324-381 of the amino acid sequence shown in SEQ ID No. 2.

Further, it is preferred that the mutant is obtained by: (1) mutating leucine at position 201 of amino acid sequence shown in SEQ ID No. 2 into phenylalanine, and the amino acid sequence of the mutant is shown in SEQ ID No.4, and the nucleotide sequence is shown in SEQ ID No.3; or (2) replacing amino acids at positions 324-381 of the amino acid sequence as shown in SEQ ID No. 2 with amino acids at positions 324-371 of the nitrilase derived from *Acidovorax facilis* CCTCC NO: M 209044 (the 324-371 amino acid sequence is shown in SEQ ID No.8, and the nucleotide sequence is shown in SEQ ID No.7), and the amino acid sequence of the mutant is shown in SEQ ID No.6, and the nucleotide sequence is shown in SEQ ID No.5.

The present invention utilized NCBI database to screen and obtain the encoding gene of a nitrilase derived from an uncultured microorganism (GenBank Accession no: AAR97494.1), in order to realize its soluble expression in prokaryotic organisms such as *Escherichia coli*, the nucleotide sequence of the nitrilase corresponding to the amino acid sequence as shown in SEQ ID No. 2 is obtained by a total synthesis method and via routine operation of genetic engineering, and shown in SEQ ID No. 1. Using site-directed mutagenesis, the amino acid sequence as shown in SEQ ID No.2 is mutated as follows: first, carry out site-directed mutagenesis of the amino acid at position 201 by PCR amplification using primers to obtain an expression vector pET-28b(+) containing the nucleotide sequence of the nitrilase mutant, introduce the expression vector into the host cell *E. coli*, subject the strain to induced expression to obtain a mutant with improved thermostability, thereby obtaining the mutant LNIT5-L201F (whose nucleotide sequence is shown in SEQ ID No.3) which is capable of efficiently catalyzing regioselective hydrolysis of dinitrile compounds to monocyanocarboxylic acid compounds.

Based on the principle of homologous recombination, firstly, design primers, use PCR amplification to obtain a nucleotide sequence that contains homologous arms and the nucleotide sequence (as shown in SEQ ID No.7) corresponding to amino acids at positions 324-371 of the nitrilase derived from *A. facilis* CCTCC NO: M 209044 (GenBank Accession no. KJ001820); then, design primers, use PCR amplification to obtain a linearized vector sequence containing homologous arms and the nucleotide sequence corresponding to amino acids at positions 1-323 of the nitrilase amino acid sequence (GenBank Accession no: AAR97494.1) derived from an uncultured microorganism; fuse the two nucleotide sequences via homologous recombination to obtain a recombinant expression vector pET-28b (+) containing the nucleotide sequence of the nitrilase fusion, introduce the vector into the host cell *E. coli*, subject the strain to induced expression to obtain a mutant with improved thermostability, thereby obtaining the mutant protein $NIT_{LNIT5-AcN}$ (whose nucleotide sequence is shown in SEQ ID No.5) which is capable of efficiently catalyzing regioselective hydrolysis of dinitrile compounds to monocyanocarboxylic acid compounds.

The present invention also relates to an encoding gene of the nitrilase mutant, a recombinant vector constructed from the encoding gene, and recombinant genetically engineered bacteria obtained by transforming the recombinant vector into the host cell. The host cell may be various conventional host cells in the field, and *E. coli* BL21 (DE3) is preferred in the present invention. Specifically, the synthesized nitrilase gene is ligated to an expression vector pET-28b(+) by enzymatic cutting and ligating to construct a recombinant expression vector pET-28b(+)-LNIT5. The present invention also provides a recombinant engineered strain containing the nitrilase LNIT5 gene above, preferably *E. coli* BL21 (DE3). The preferred recombinant engineered strain is obtained by transforming the recombinant expression vector pET-28b(+)-LNIT5 above into the host cell *E. coli* BL21 (DE3).

The present invention also provides an application of the nitrilase mutant in catalyzing a dinitrile compound to prepare a monocyanocarboxylic acid compound, specifically, the application is carried out as follows: use wet cells, wet cell-immobilized cells or purified nitrilase as a catalyst, 1-cyanocyclohexylacetonitrile as a substrate, and pH=7.0, 200 M disodium hydrogen phosphate-sodium dihydrogen phosphate buffer as a reaction medium, carry out the reaction in 45° C. constant temperature water bath, after the reaction is completed, subject the reaction solution to separation and purification to obtain 1-cyanocyclohexyl acetic acid; in which, the wet wells are obtained by fermentation culture of the genetically engineered strain containing the encoding gene of the nitrilase mutant, the purified nitrilase is obtained by subjecting the wet cells to ultrasonic breaking and then extraction, the final concentration of the substrate calculated by the volume of the buffer is 100~1300 mM (preferably 1000 mM) and the amount of the catalyst calculated by the weight of the wet cells is 10~100 g/L buffer (preferably 50 g/L).

Further, the catalyst is prepared according to one of the following methods: (1) the genetic engineered strain containing the encoding gene of the nitrilase mutant is inoculated into LB medium, cultured at 37° C. for 10-12 hours, the resulting inoculum is inoculated to LB medium containing kanamycin (with the final concentration of 50 mg/L) with 2% incubating volume, amplified and cultured at 37° C.; when $OD_{600}$ of the culture medium reaches 0.6-0.8, isopropyl-β-D-thiogalactopyranoside (IPTG) is added with the final concentration of 0.1 mM, and the bacteria solution is subjected to induced expression at 28° C. for 10 hours; the wet cells are harvested by centrifugation and washed with normal saline twice; (2) the wet cells obtained in step (1) are resuspended with 50 mM $NaH_2PO_4$ buffer (pH 8.0) containing NaCl with the final concentration of 300 mM, ultrasonic broken (400 W, 15 min, 1 s breaking, 1 s pause), and followed by centrifugation at 12,000×g for 20 min to remove cell debris, the resulting supernatant is a crude enzyme solution; the crude enzyme solution is applied onto the Ni-NTA column which has been washed with equilibrium buffer at a flow rate of 1 mL/min, the weakly adsorbed protein impurities are eluted with elution buffer at a flow rate of 2 mL/min; then the target protein is eluted with protein elution buffer at a flow rate of 2 mL/min and collected; finally, the obtained target protein is dialyzed with a sodium chloride aqueous solution with the mass concentration of 0.9% as the dialysate, and the retention is purified nitrilase; wherein the equilibrium buffer is 50 mM $NaH_2PO_4$ buffer (pH 8.0) containing NaCl with the final concentration of 300 mM, the elution buffer is 50 mM $NaH_2PO_4$ buffer (pH 8.0) containing NaCl and imidazole with the final concentrations of 300 mM and 50 mM, and the protein elution buffer is 50 mM $NaH_2PO_4$ buffer (pH 8.0) containing NaCl and imidazole with the final concentrations of 300 mM and 250 mM.

The nitrilase mutant of the present invention may be the recombinant expression transformant (that is, wet cell, preferably *E. coli* BL21 (DE3)) containing the nitrilase mutant gene, the unpurified crude enzyme, or the purified pure enzyme. If needed, it can be used after immobilization.

In the present application, the final concentrations of the components of Luria-Bertani (LB) liquid medium are as follows: 10 g/L tryptone, 5 g/L yeast extract, 10 g/L sodium chloride, water as solvent, natural pH.

The final mass concentrations of the components of LB solid medium are as follows: 10 g/L tryptone, 5 g/L yeast extract, 10 g/L sodium chloride, 1.5% agar, water as solvent, natural pH.

Compared with prior art, advantages of the present invention are mainly embodied in: in the present invention, by the protein molecular modification, thermostability of the purified nitrilase LNIT5 is increased by up to 4.5 folds; and by utilizing recombinant *E. coli* containing the nitrilase mutant to hydrolyze 1-cyanocyclohexylacetonitrile at a high temperature (45° C.), product tolerance is increased, activity of NIT5-L201F is increased by 20%, and the mutant $NIT_{LNIT5-AcN}$ can completely hydrolyze 750 mM 1-cyanocyclohexylacetonitrile within 8 hours and achieve an doubled conversion rate. Therefore, the mutants obtained by the present invention have a good application prospect in efficiently catalyzing 1-cyanocyclohexylacetonitrile to synthesize gabapentin intermediate, 1-cyanocyclohexyl acetic acid.

SPECIFIC EMBODIMENT

Figure 1:
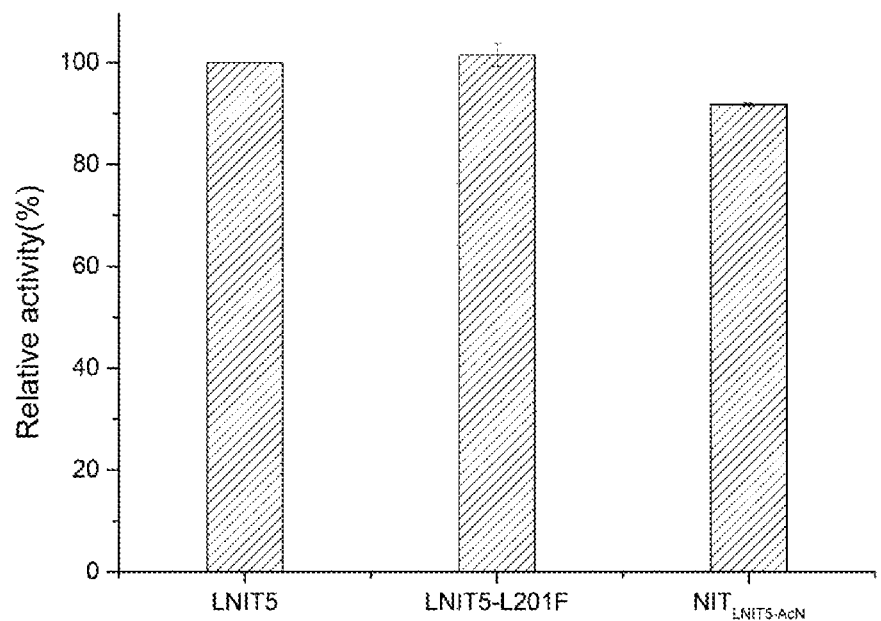
FIG. 1: comparison of activities of the purified nitrilase mutants.

The present invention is further illustrated below with specific examples, but protection scope of the present invention is not limited to these examples:

Example 1: Acquisition of Nitrilase LNIT5

According to protein NCBI database, BLAST was run by using a nitrilase derived from *A. facilis* CCTCC NO: M 209044 as a template, and a nitrilase gene (GenBank Accession no: AAR97494.1) was screened from the results. The screened nitrilase is derived from an uncultured microorganism, and 76% similar to the nitrilase derived from *A. facilis* CTCCC NO: M 209044. According to the amino acid sequence of the screened nitrilase and codons which *Escherichia coli* prefers, codon optimization was carried out, the amino acid sequence of the nitrilase LNIT5 is shown in SEQ ID No. 2, and the nucleotide sequence encoding the enzyme is shown in SEQ ID No. 1.

Example 2: Construction of Recombinant Expression Vector pET-28b(+)-LNIT5 and the Recombinant Strain The recombinant expression vector pET-28b(+)-LNIT5 containing the nitrilase LNIT5 gene was synthesized by the total-synthetic method and via conventional operation of genetic engineering. The constructed expression vector pET-28b(+)-LNIT5 was transferred into a receptor strain, *E. coli* BL21 (DE3), which was then plated on a LB agar plate containing kanamycin (at the final concentration of 50 μg/mL) and cultured overnight at 37° C. The colonies grown on the plate were randomly selected, and the plasmid was extracted and identified by agarose gel electrophoresis to obtain the recombinant strain *E. coli* BL21 (DE3)/pET-28b (+)-LNIT5.

Table 1 Primer Design Table

TABLE 1 primer design table

| Primer name | Primer sequence (5' to 3') |
| --- | --- |
| L201F-f | CCGGACGTTCCGCAGTTTGGCGCAGGTGCGAATG (SEQ ID NO: 9) |
| L201F-r | CATTCGCACCTGCGCCAAACTGCGGAACGTCCGG (SEQ ID NO: 10) |
| I-f | ACCTGGACGAAGAAGGTCGTCTGGATGTTAACAC GCGTTCC (SEQ ID NO: 11) |
| I-r | TTGTTAGCAGCCGGATCTCAGTGGTGGTGGTGGT GGTGC (SEQ ID NO: 12) |
| P-f | TGAGATCCGGCTGCTAACAAA (SEQ ID NO: 13) |
| P-r | ACGACCTTCTTCGTCCAGGTAA (SEQ ID NO: 14) |

Example 3: Construction of Nitrilase LNIT5 Mutant

The expression plasmid pET-28b(+)-LNIT5 was used as a template, and the site-directed mutagenesis was carried out by amplification of the whole plasmid. The PCR system (50 μL) was as follows: 0.5-20 ng of the template, 10-15 pmol of each primer (L201F-f (SEQ ID NO:9) and L201F-r (SEQ ID NO:10), whose sequences is seen in in table 1), 5×PrimeSTAR Buffer ($Mg^{2+}$ plus), 0.2 mM dNTP, and 1.25 U PrimeSTAR HS DNA Polymerase. The PCR program was as follows: (1) pre-denaturation at 98° C. for 3 min; (2) denaturation at 98° C. for 10 s; (3) anneal at 60° C. for 5 s; (4) extension at 72° C. for 6.5 min, wherein steps (2)-(4) were cycled 30 times; and (5) finally, extension at 72° C. for 5 min, preservation at 4° C. The PCR product was identified by agarose gel electrophoresis, digested with DpnI, and then introduced into the host strain *E. coli* BL21 (DE3), which was then plated on a LB plate containing 50 μg/mL kanamycin to obtain monoclones. The selected monoclonal plasmid was extracted, and sequenced and verified by Beijing TSINGKE Biological Technology CO., LTD. to obtain the mutant LNIT5-L201F (the amino acid sequence of the mutant is shown in SEQ ID No.4, and the nucleotide sequence is shown in SEQ ID No.3), whose amino acid sequence was shown in SEQ ID No. 4, and nucleotide sequence was shown in SEQ ID. No.3.

Using the recombinant expression plasmid pET-28b(+)-AcN containing the nitrilase AcN gene derived from *A. facilis* CTCCC NO: M 209044 as a template, the nucleotide sequence containing homologous arms and the nucleotide sequence corresponding to the amino acids at the C-terminal positions 324-381 of the nitrilase AcN (the amino acid sequence of the amino acids at positions 324-381 is shown in SEQ ID No. 8, and the nucleotide sequence is shown in SEQ ID No. 7) was obtained by PCR amplification. The PCR system (50 μL) was as follows: 0.5-20 ng of the template, 10-15 pmol of each of primers I-f (SEQ ID NO:11) and I-r (SEQ ID NO:12), 5×PrimeSTAR Buffer ($Mg^{2+}$ plus), 0.2 mM dNTP, and 1.25 U PrimeSTAR HS DNA Polymerase. The PCR program was as follows: (1) pre-denaturation at 98° C. for 3 min; (2) denaturation at 98° C. for 10 s; (3) anneal at 60° C. for 5 s; (4) extension at 72° C. for 10 s, wherein steps (2)~(4) were cycled 30 times; and (5) finally, extension at 72° C. for 5 min, preservation at 4° C. The obtained PCR product was separated by agarose gel electrophoresis, and about 150 bp DNA fragments were recovered for use.

Using the expression plasmid pET-28b(+)-LNIT5 as a template, a pET-28b(+) linear vector plasmid containing homologous arms and the nucleotide sequence corresponding to amino acids at the N-terminal positions 1-323 of the nitrilase LNIT5 was obtained by PCR amplification. The PCR system (50 μL) was as follows: 0.5-20 ng of the template, 10-15 pmol of each of primers P-f (SEQ ID NO:13) and P-r (SEQ ID NO:14), 5×PrimeSTAR Buffer ($Mg^{2+}$ plus), 0.2 mM dNTP, and 1.25 U PrimeSTAR HS DNA Polymerase. The PCR program was as follows: (1) pre-denaturation at 98° C. for 3 min; (2) denaturation at 98° C. for 10 s; (3) anneal at 60° C. for 5 s; (4) extension at 72° C. for 6.5 min, wherein steps (2)-(4) were cycled 30 times; and (5) finally, extension at 72° C. for 5 min, preservation at 4° C. The PCR product was verified by agarose gel electrophoresis, digested with restriction endonuclease DpnI, and the target fragments were obtained by PCR purification kit.

Finally, homologous recombination was achieved using the ClonExpress® II One Step Cloning Kit (Vazyme Biotech Co., Ltd., Nanjing). The expression plasmid containing the fusion protein was introduced into the host strain *E. coli* BL21 (DE3), which was then plated onto a LB plate containing 50 μg/mL kanamycin to obtain monoclones. The selected monoclonal plasmid was extracted, and sequenced and verified by Beijing TSINGKE Biological Technology CO., LTD. to obtain fusion protein $NIT_{LNIT5-AcN}$, whose amino acid sequence was shown in SEQ ID No. 6, and nucleotide sequence was shown in SEQ ID No. 5.

Example 4: Expression of the Wild-Type or the Mutant-Type Nitrilase

The transformants *E. coli* BL21 (DE3)/pET-28b(+)-LNIT5, *E. coli* BL21 (DE3)/pET-28b(+)-LNIT5-L201F and *E. coli* BL21 (DE3)/pET-28b(+)-$NIT_{LNIT5-AcN}$ obtained in example 2 and example 3 were respectively inoculated into LB medium, cultured at 37° C. for 10-12 hours, the resulting inocula were respectively inoculated to LB medium containing kanamycin (with the final concentration of 50 mg/L) with 2% incubating volume, amplified and cultured at 37° C. When $OD_{600}$ of the culture medium reached 0.6-0.8, isopropyl-β-D-thiogalactopyranoside (IPTG) was added with the final concentration of 0.1 mM, and the bacteria solution was subjected to induced expression at 28° C. for 10 hours. The wet cells were harvested by centrifugation and washed with normal saline twice.

Example 5: Purification of the Wild-Type or the Mutant-Type Nitrilase (1) 50 mM $NaH_2PO_4$ buffer (pH 8.0) containing 300 mM NaCl was added to the wet cells obtained in example 4, the cells were resuspended, ultrasonic broken (400 W, 15 min, 1 s breaking, 1 s pause) and followed by centrifugation at 12,000×g for 20 min to remove cell debris. The supernatant was a crude enzyme solution for separation and purification.

(2) After pre-filling the 20 mL Ni-NTA affinity column, equilibration was performed using equilibrium buffer (50 mM $NaH_2PO_4$, 300 mM NaCl, pH 8.0) at a flow rate of 2 mL/min.

(3) After the Ni-NTA column was washed with 8-10 column volume, the obtained crude enzyme solution was applied onto the Ni-NTA column at a flow rate of 1 mL/min, and the target protein bound to the column. After loading, a large amount of unbound protein impurities which did not bind to the resin would be directly removed.

(4) The weakly adsorbed protein impurities were eluted with elution buffer (50 mM $NaH_2PO_4$, 300 mM NaCl, 50 mM imidazole, pH 8.0) at a flow rate of 2 mL/min.

(5) The target protein was eluted with protein elution buffer (50 mM $NaH_2PO_4$, 300 mM NaCl, 250 mM imidazole, pH 8.0) at a flow rate of 2 mL/min and collected.

(6) The collected enzyme solution was dialyzed using a dialysis bag (Economical Biotech Membrane, 14 KD, 34 mm Width, purchased from Sangon Biotech (Shanghai) Co., Ltd.) with a sodium chloride aqueous solution with the mass concentration of 0.9% as the dialysate, and the retention was purified nitrilase.

(7) The purified proteins were analyzed by SDS-PAGE.

Example 6: Determination of Activity of the Purified Nitrilases

The activity of the purified nitrilases from example 5 was determined. A reaction system (10 mL) for nitrilase activity assay was as follows: sodium dihydrogen phosphate-disodium hydrogen phosphate buffer (100 mM, pH 7.0), 200 mM 1-cyanocyclohexylacetonitrile, and 75 mg of the purified nitrilase. The reaction solution was preheated at 45° C. for 10 min and then reacted at 150 rpm for 10 min. 500 μL of the supernatant was sampled, and 500 μL of 2 M HCl was added to terminate the reaction, and the conversion rate of 1-cyanocyclohexyl acetic acid was determined by liquid chromatography (Shimadzu LC-16) external standard method. The column is)(Bridge BEH C18 Column (130 A, 5 μm, 4.6 mm×250 mm, 1/pkg, Waters), and the mobile phase was a buffer (0.58 g/L diammonium phosphate, 1.83 g/L sodium perchlorate, pH was adjusted to 1.8 by perchloric acid) and acetonitrile in a ratio of 76:24 (v/v), the flow rate was 1 mL/min, the ultraviolet detection wavelength was 215 nm, and the column temperature was 40° C. Enzyme activity definition (U): the amount of enzyme required to catalyze the formation of 1 μmol of 1-cyanocyclohexyl acetic acid per minute at 45° C., in pH 7.0, 100 mM sodium dihydrogen phosphate-disodium hydrogen phosphate buffer was defined as 1 U. The results were shown in FIG. 1.

Example 7: Determination of Thermostability of the Wild-Type or the Mutant-Type Nitrilase at 45° C.

The thermostability of the purified nitrilases from example 5 was measured. A certain amount of the purified nitrilase was taken into a 50 mL sterile polypropylene centrifuge tube and stored in a 45° C. constant temperature water bath. The protein was sampled for measurement of activity of the protein at different time intervals according to the method as described in example 6. With the activity of the protein before stored in a 45° C. constant temperature water bath as a control, residual activities of the protein at every time interval were calculated.

Figure 2:
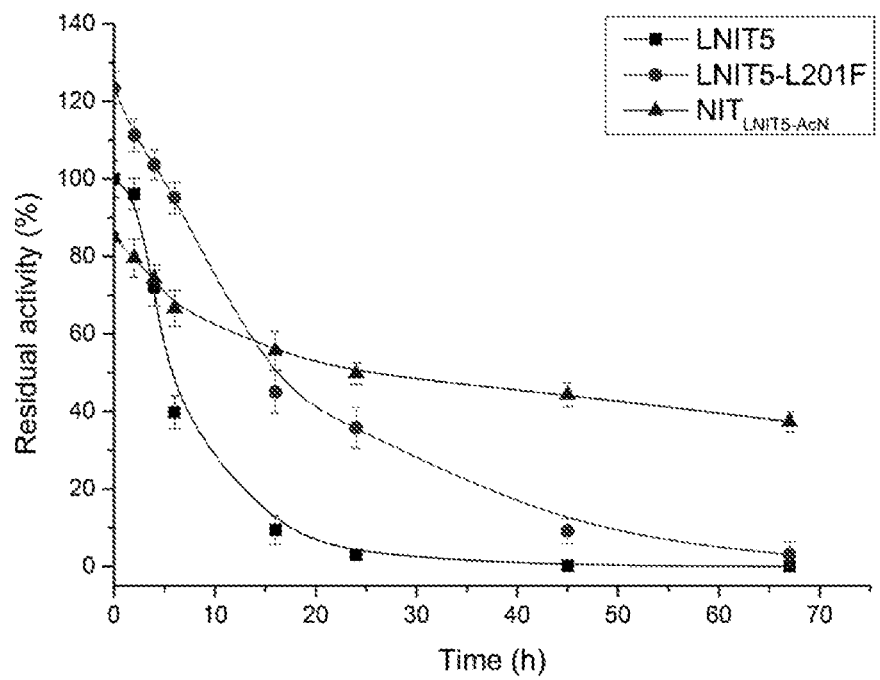
FIG. 2: thermal stability of the nitrilase mutants at 45° C.

As shown in FIG. 2, the half-life of the original nitrilase LNIT5 was determined to be 6 h, the half-life of the mutant LNIT5-L201F (the amino acid sequence is shown in SEQ ID No.4, and the nucleotide sequence is shown in SEQ ID No.3) was 16 h, and the half-life of the fusion protein NIT$_{LNIT5-AcN}$ (the amino acid sequence is shown in SEQ ID No:6, and the nucleotide sequence is shown in SEQ ID No:5) was 27 h.

Figure 3:
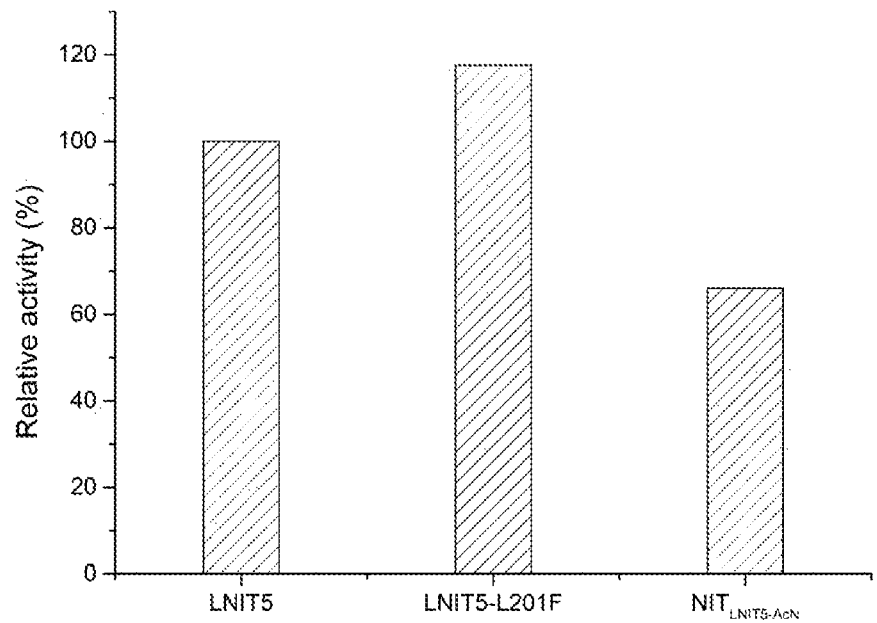
FIG. 3: comparison of activity of *E. coli* resting cells containing the nitrilase mutants.

Example 8: Determination of Activity of Recombinant E. coli Containing the Wild-Type or the Mutant-Type Nitrilase The nitrilase activities of recombinant *E. coli* containing the wild-type or the mutant-type nitrilase *E. coli* BL21 (DE3)/pET-28b(+)-LNIT5, *E. coli* BL21 (DE3)/pET-28b (+)-LNIT5-L201F and *E. coli* BL21(DE3)/pET-28b(+)-NIT$_{LNIT5-AcN}$ obtained in example 4 were measured. A reaction system (10 mL) for nitrilase activity assay was as follows: sodium dihydrogen phosphate-disodium hydrogen phosphate buffer (200 mM, pH 7.0), 1-cyanocyclohexylacetonitrile with the final concentration of 100 mM, 10 g/L of the *E. coli* wet cells. The reaction solution was preheated at 45° C. for 10 min and then reacted at 150 rpm for 10 min. 500 μL of the supernatant was sampled, and conversion rate of 1-cyanocyclohexyl acetic acid was measured by liquid chromatography (Shimadzu LC-16) external standard method. The conditions of liquid chromatography were described in example 6, and the results were shown in FIG. 3.

Example 9: Determination of Thermostability of Recombinant E. coli Containing the Wild-Type or the Mutant-Type Nitrilase at 45° C.

The resting cells of the recombinant *E. coli* containing the wild-type or the mutant-type nitrilase, *E. coli* BL21 (DE3)/pET-28b(+)-LNIT5, *E. coli* BL21 (DE3)/pET-28b(+)-LNIT5-L201F and *E. coli* BL21(DE3)/pET-28b(+)-NIT$_{LNIT5-AcN}$, obtained in example 4, were respectively suspended in sodium dihydrogen phosphate-disodium hydrogen phosphate buffer (200 mM, pH 7.0) to obtain a 20 g/L bacterial suspension, and stored in a 45° C. constant temperature water bath. The bacterial suspension was sampled for measurement of activity of the resting cells at different time intervals according to the method as described in example 8. With the activity of the resting cells before stored in a 45° C. constant temperature water bath as a control, residual activities of the resting cells at each time interval were calculated, and the results were shown in table 2.

TABLE 2

Thermostability of *E. coli* resting cells containing the nitrilase mutants at 45° C.

| Mutants | Residual activity after 14 hours | Residual activity after 24 hours |
| --- | --- | --- |
| *E. coli* BL21 (DE3)/pET-28b(+)-LNIT5 | 71.5% | 40% |
| *E. coli* BL21 (DE3)/pET-28b(+)-LNIT5-L201F | 96.8% | 78% |
| *E. coli* BL21 (DE3)/pET-28b(+)-NIT$_{LNIT5-AcN}$ | 98.5% | 89% |
| *E. coli* BL21 (DE3) | 0 | 0 |
| *E. coli* BL21 (DE3)/pET-28b(+) | 0 | 0 |

Example 10: Hydrolysis of 400 mM 1-Cyanocycloalkaneacetonitrile by Recombinant E. coli Containing the Wild-Type or the Mutant-Type Nitrilase 0.5 g of wet cells of *E. coli* BL21 (DE3)/pET-28b(+)-LNIT5, *E. coli* BL21 (DE3)/pET-28b(+)-LNIT5-L201F and *E. coli* BL21(DE3)/pET-28b(+)-NIT$_{LNIT5-AcN}$, obtained by the method as described in example 4, were suspended in 10 mL of sodium dihydrogen phosphate-disodium hydrogen phosphate buffer (200 mM, pH 7.0) respectively, 0.592 g of 1-cyanocyclohexylacetonitrile was added with the final concentration of 400 mM, and the reaction was carried out in a 45° C. constant temperature water bath. Samples were taken at different times, centrifuged at 12000 rpm, and the precipitates were discarded. The treated reaction solutions were analyzed for profiling the product concentration by high performance liquid chromatography. The HPLC conditions were as described in example 6.

Figure 4:
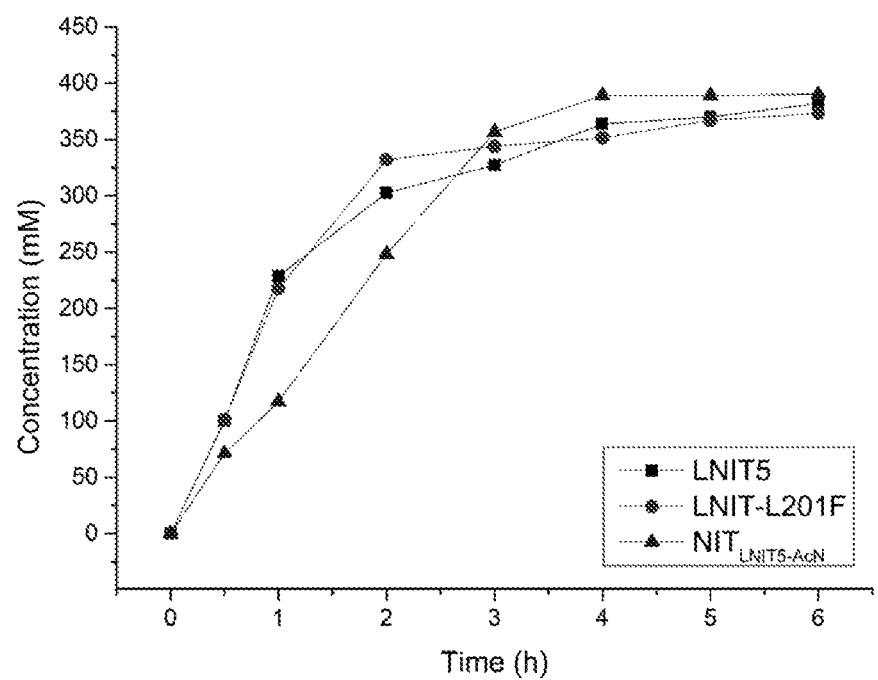
FIG. 4: comparison of hydrolysis of 400 mM 1-cyanocycloalkaneacetonitrile by recombinant *E. coli* resting cells containing the nitrilase mutants.

As shown in FIG. 4, *E. coli* BL21 (DE3)/pET-28b(+)-LNIT5, *E. coli* BL21 (DE3)/pET-28b(+)-LNIT5-L201F and *E. coli* BL21 (DE3)/pET-28b(+)-NIT$_{LNIT5-AcN}$ could completely hydrolyze the substrate within 6 h, wherein the reaction catalyzed by *E. coli* BL21 (DE3)/pET-28b(+)-NIT$_{LNIT5-AcN}$ was faster than that catalyzed by *E. coli* BL21 (DE3)/pET-28b(+)-LNIT5.

Example 11: Hydrolysis of 750 mM 1-Cyanocycloalkaneacetonitrile by Recombinant E. coli Containing the Nitrilase Mutant NIT$_{LNIT5-AcN}$ (Amino Acid Sequence is Shown in SEQ ID No:6, and Nucleotide Sequence is Shown in SEQ ID No:5)

0.5 g of the *E. coli* BL21 (DE3)/pET-28b(+)-NIT$_{LNIT5-AcN}$ wet cells obtained by the method as described in example 4, were suspended in 10 mL of sodium dihydrogen phosphate-disodium hydrogen phosphate buffer (200 mM, pH 7.0), 1.11 g of 1-cyanocyclohexylacetonitrile was added with the final concentration of 0.75 M, and the reaction was carried out in 45° C. constant temperature water bath. Samples were taken at different times, centrifuged at 12000 rpm for 3 min, and the precipitates were discarded. The treated reaction solution was analyzed for profiling the product concentration by high performance liquid chromatography. The HPLC conditions were as described in example 6.

Figure 5:
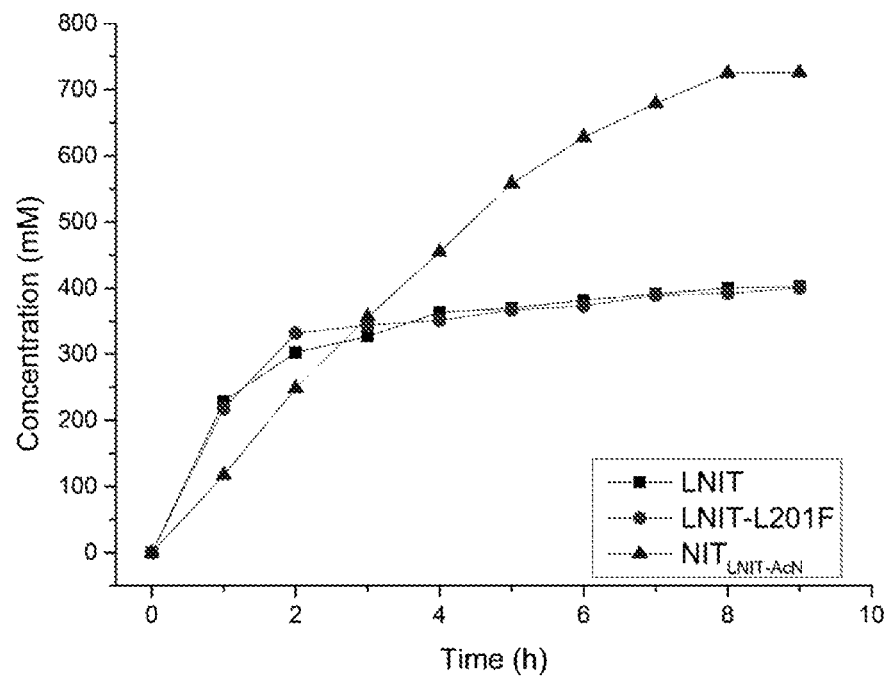
FIG. 5: comparison of hydrolysis of 750 mM 1-cyanocycloalkaneacetonitrile by recombinant *E. coli* resting cells containing the nitrilase mutants.

As shown in FIG. 5, the mutant, *E. coli* BL21 (DE3)/pET-28b(+)-NIT$_{LNIT5-AcN}$, could completely hydrolyze the substrate within 8 h, much faster than *E. coli* BL21 (DE3)/pET-28b(+)-LNIT5.

Example 12: Hydrolysis of 1.0 M 1-Cyanocycloalkaneacetonitrile by Recombinant E. coli Containing the Nitrilase Mutant NIT$_{LNIT5-AcN}$ (Amino Acid Sequence is Shown in SEQ ID No:6, and Nucleotide Sequence is Shown in SEQ ID No:5)

0.5 g of the *E. coli* BL21 (DE3)/pET-28b(+)-NIT$_{LNIT5-AcN}$ wet cells obtained by the method as described in example 4, were suspended in 10 mL of sodium dihydrogen phosphate-disodium hydrogen phosphate buffer (200 mM, pH 7.0), 1.48 g of 1-cyanocyclohexylacetonitrile (at a final concentration of 1.0M) was added, and the reaction was carried out in 45° C. constant temperature water bath. Samples were taken at different times, centrifuged at 12000 rpm for 3 min, and the precipitates were discarded. The treated reaction solution was analyzed for profiling the product concentration by high performance liquid chromatography. The analysis conditions of HPLC were as described in example 6.

Figure 6:
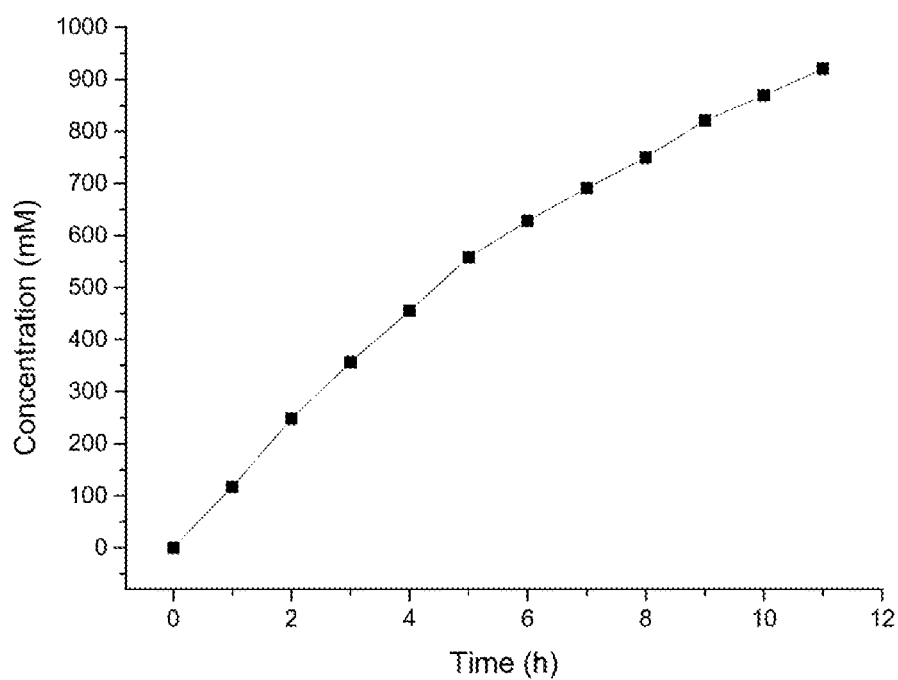
FIG. 6: hydrolysis of 1.0 M 1-cyanocycloalkaneacetonitrile by recombinant *E. coli* resting cells containing the nitrilase mutant $NIT_{LNIT5-AcN}$ (nucleotide sequence is shown in SEQ ID No:5).
Figure 7:
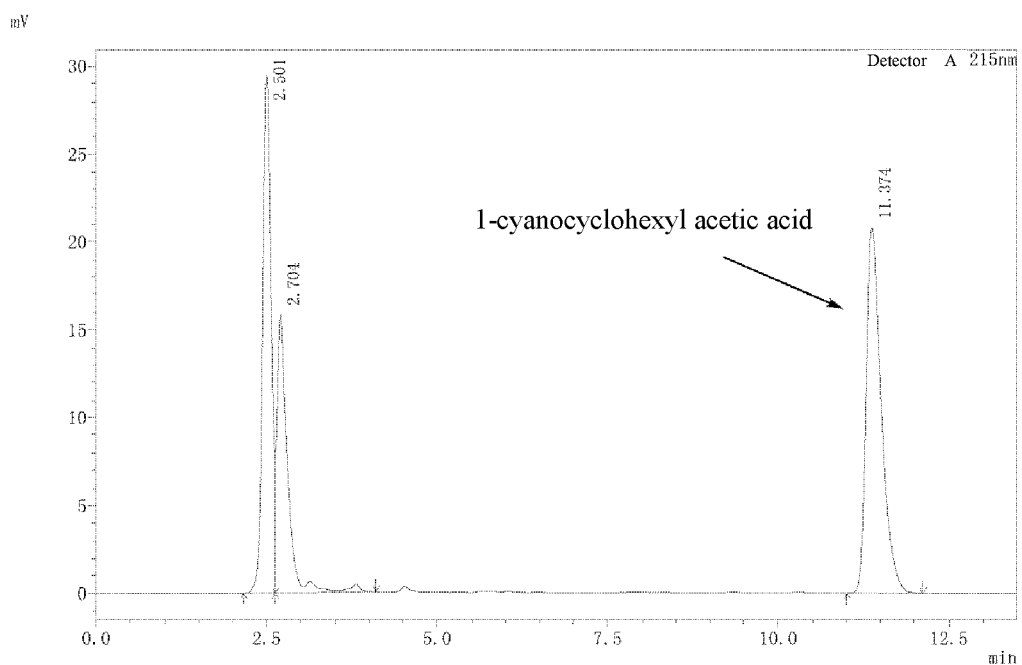
FIG. 7: high performance liquid chromatogram of 1-cyanocyclohexyl acetic acid.

As shown in FIG. 6, the mutant, *E. coli* BL21 (DE3)/pET-28b(+)-NIT$_{LNIT5-AcN}$, could completely hydrolyze the substrate within 11 h.

Example 13: Hydrolysis of 750 mM 1-Cyanocycloalkaneacetonitrile by the Immobilized Cells 2 g of the *E. coli* BL21 (DE3)/pET-28b(+)-NIT$_{LNIT5-AcN}$ wet cells obtained by the method as described in example 4, were suspended in 20 mL of sodium dihydrogen phosphate-disodium hydrogen phosphate buffer (200 mM, pH 7.0), diatomite was added into the suspension with the final concentration of 0.006 g/mL, and the mixture was stirred at room temperature for 1 h. Subsequently, polyethyleneimine (added in the form of a 5% (w/w) aqueous solution) was added into the mixture with the final concentration of 3% (v/v), and stirred at room temperature for 1 hour. Finally, glutaraldehyde (added in the form of a 25% (w/w) aqueous solution) was added with the final concentration of 1% (v/v) and the mixture was stirred for 1 hour, and the immobilized cells were obtained by vacuum filtration.

All the immobilized cells obtained above (the amount of the immobilized cells was 100 g/L calculated by resting cells) were suspended in 20 mL of disodium hydrogen phosphate-sodium dihydrogen phosphate buffer system (200 mM, pH=7.0), 2.22 g of 1-cyanocyclohexylacetonitrile were added with the final concentration of 750 mM, and the reaction was carried out in 45° C. constant temperature water bath for 8 hours per batch. After the completion of each batch of the reaction, vacuum filtration was carried out for the solid-liquid separation, and the resulting reaction solution was analyzed by high performance liquid chromatography for profiling the concentration of the product according to the method described in example 6, and the recovered immobilized cells were applied into the next batch of reaction. As a result, the prepared immobilized cells were reused for 6 batches, and the conversion rate of each batch was more than 99%.

The invention claimed is:

1. A nitrilase mutant having the amino acid sequence of SEQ ID No:6.

2. A method for catalyzing 1-cyanocyclohexylacetonitrile to 1-cyanocyclohexyl acetic acid, comprising providing the nitrilase mutant of claim 1 as a catalyst.

3. The method of claim 2, further comprising:
providing wet cells, wet cell-immobilized cells or purified nitrilase mutant as the catalyst, 1-cyanocyclohexylacetonitrile as a substrate, and pH=7.0, 200 M disodium hydrogen phosphate-sodium dihydrogen phosphate buffer as a reaction medium,
carrying out the reaction in a 45° C. constant temperature water bath,
after the reaction is completed, subjecting the reaction solution to separation and purification to obtain 1-cyanocyclohexyl acetic acid,
wherein the wet cells are obtained by fermenting culture of genetically engineered cells containing a gene encoding the nitrilase mutant, and the purified nitrilase mutant is obtained by subjecting the wet cells to ultrasonic breaking and then extraction.

4. The method of claim 3, wherein in the reaction system, a final concentration of the substrate calculated by a volume of the buffer is 100~1300 mM, and an amount of the catalyst calculated by a weight of the wet cells is 10~100 g/L buffer.

5. The method of claim 3, wherein the catalyst is prepared according to one of the following methods:

(1) genetically engineered cell containing the gene encoding the nitrilase mutant is inoculated into a LB medium and cultured at 37° C. for 10-12 hours, then the resulting inoculum is inoculated with 2% incubating volume to a LB medium containing kanamycin with a final concentration of 50 mg/L, amplified and cultured at 37° C.; when OD600 of the culture medium reaches 0.6-0.8, isopropyl-β-D-thiogalactopyranoside is added with a final concentration of 0.1 mM, and the bacteria solution is subjected to induced expression at 28° C. for 10 hours; the wet cells are harvested by centrifugation and washed with normal saline twice;

(2) the wet cells obtained in step (1) are resuspended with 50 mM $NaH_2PO_4$ buffer (pH 8.0) containing NaCl with a final concentration of 300 mM, ultrasonic broken, and followed by centrifugation to remove cell debris, the resulting supernatant is a crude enzyme solution; the crude enzyme solution is applied onto the Ni-NTA column which has been washed with equilibrium buffer at a flow rate of 1 mL/min, then the weakly adsorbed protein impurities are eluted with elution buffer at a flow rate of 2 mL/min; then the target protein is eluted with protein elution buffer at a flow rate of 2 mL/min and collected; finally, the obtained target protein is dialyzed with a sodium chloride aqueous solution with a mass concentration of 0.9% as the dialysate, and the retention is purified nitrilase mutant; in which the equilibrium buffer is 50 mM $NaH_2PO_4$ buffer (pH 8.0)

containing NaCl with a final concentration of 300 mM, the elution buffer is 50 mM $NaH_2PO_4$ buffer (pH 8.0) containing NaCl and imidazole with a final concentrations of 300 mM and 50 mM, and the protein elution buffer is 50 mM $NaH_2PO_4$ buffer (pH 8.0) containing NaCl and imidazole with a final concentrations of 300 mM and 250 mM; or (3) the wet cells of the step (1) are suspended in 200 mM sodium dihydrogen phosphate-disodium hydrogen phosphate buffer system (pH 7.0), diatomite is added into the suspension with a final concentration of 0.006 g/mL, and the mixture is stirred at room temperature for 1 h; subsequently, polyethyleneimine is added into the mixture with a final volume concentration of 3%, and the mixture is stirred at room temperature for 1 hour; finally, glutaraldehyde is added with a final volume concentration of 1% and the mixture is stirred for 1 hour, and the immobilized cells are obtained by vacuum filtration; in which, the polyethyleneimine is added in a form of a aqueous solution with a mass concentration of 5%, and the glutaraldehyde is added in a form of a aqueous solution with a mass concentration of 25%.

\* \* \* \* \*

SEQUENCE LISTING

```
<160> NUMBER OF SEQ ID NOS: 14

<210> SEQ ID NO 1
<211> LENGTH: 1146
<212> TYPE: DNA
<213> ORGANISM: Unknown
<220> FEATURE:
<223> OTHER INFORMATION: soil sample

<400> SEQUENCE: 1
atgctgactt ataaaggcgt tttcaaagcc gctactgttc aggcggaacc ggtgtggatg      60
gacgcagacg cgaccatcac caaagctatc cgtattattg aagaagctgc ggacaacggt     120
gcaaaatttg tagcgtttcc tgaagttttc attccaggtt atccgtggtg gatctggctg     180
ggcaccgcga tgtggggtgc gaagttcgtg gtaccgttcc atgaaaactg tctggaactg     240
ggcgataagc gtatgcagcg cattcaggcc gccgcgaaac aaaatggcat cgcactggta     300
atgggctacg gtgaacgcga cggtggtagc cgttacatga gccaggtgtt catcgatgac     360
agcggtaaaa tcgtggcgaa tcgccgtaag ctgaaaccaa ctcacgaaga gcgtaccatt     420
ttcggtgaag gtaacggttc tgatttcatc acgcatgatt tcccttttcgc tcgcgttggt     480 ggttttaatt gctgggaaca cctgcagccg ctgagcaaat acatgatgta tagcctgcaa     540
gaacaggtgc atgtcgcctc ttggccggca atgtgtactt accagccgga cgttccgcag     600
ctgggcgcag gtgcgaatga ggcagtgacg cgttcttacg ccatcgaagg tgcgtgctac     660
gttctgggtg ctacgctggt tattggtaag gcggcgcacg atgcattttg cgataccgaa     720
gaacaccaca aactgctggg catgggtggc ggttgggcgc gcatcttcgg tccggacggt     780
gaatatctgg ctgaaagcct ggctcacgac gcagagggta tcctgtacgc cgatattgac     840
ctgtctaaaa tcctgctggc aaaagctaac accgacacgt tcggtcatta tgcacgtccg     900
gatgtcctgt ccctgctggt taacacccac aaccctggtc cggtacgtta cctggacgaa     960
gaaggtcgtc aggtgagcac tagcatccgt cgccacgaaa aactggaggg tcaatctctg    1020
gacctggagg ttactccggc gaccccggcc accctggaca tcgcatctct ggttcagcag    1080
gctaaaccgt ctactgttaa atctgagtcc aacgccagca cgaaacagcc ggacctggcg    1140
gtataa                                                              1146

<210> SEQ ID NO 2
<211> LENGTH: 381
<212> TYPE: PRT
<213> ORGANISM: Unknown
<220> FEATURE:
<223> OTHER INFORMATION: soil sample
```

```
<400> SEQUENCE: 2

Met Leu Thr Tyr Lys Gly Val Phe Lys Ala Ala Thr Val Gln Ala Glu
1               5                   10                  15

Pro Val Trp Met Asp Ala Asp Ala Thr Ile Thr Lys Ala Ile Arg Ile
            20                  25                  30

Ile Glu Glu Ala Ala Asp Asn Gly Ala Lys Phe Val Ala Phe Pro Glu
                35                  40                  45

Val Phe Ile Pro Gly Tyr Pro Trp Trp Ile Trp Leu Gly Thr Ala Met
        50                  55                  60

Trp Gly Ala Lys Phe Val Val Pro Phe His Glu Asn Cys Leu Glu Leu
65                  70                  75                  80

Gly Asp Lys Arg Met Gln Arg Ile Gln Ala Ala Lys Gln Asn Gly
                85                  90                  95

Ile Ala Leu Val Met Gly Tyr Gly Glu Arg Asp Gly Ser Arg Tyr
                100                 105                 110

Met Ser Gln Val Phe Ile Asp Asp Ser Gly Lys Ile Val Ala Asn Arg
        115                 120                 125

Arg Lys Leu Lys Pro Thr His Glu Glu Arg Thr Ile Phe Gly Glu Gly
        130                 135                 140

Asn Gly Ser Asp Phe Ile Thr His Asp Phe Pro Phe Ala Arg Val Gly
145                 150                 155                 160

Gly Phe Asn Cys Trp Glu His Leu Gln Pro Leu Ser Lys Tyr Met Met
                165                 170                 175

Tyr Ser Leu Gln Glu Gln Val His Val Ala Ser Trp Pro Ala Met Cys
        180                 185                 190

Thr Tyr Gln Pro Asp Val Pro Gln Leu Gly Ala Gly Ala Asn Glu Ala
        195                 200                 205

Val Thr Arg Ser Tyr Ala Ile Glu Gly Ala Cys Tyr Val Leu Gly Ala
        210                 215                 220

Thr Leu Val Ile Gly Lys Ala Ala His Asp Ala Phe Cys Asp Thr Glu
225                 230                 235                 240

Glu His His Lys Leu Leu Gly Met Gly Gly Gly Trp Ala Arg Ile Phe
                245                 250                 255

Gly Pro Asp Gly Glu Tyr Leu Ala Glu Ser Leu Ala His Asp Ala Glu
            260                 265                 270

Gly Ile Leu Tyr Ala Asp Ile Asp Leu Ser Lys Ile Leu Leu Ala Lys
            275                 280                 285

Ala Asn Thr Asp Thr Val Gly His Tyr Ala Arg Pro Asp Val Leu Ser
    290                 295                 300

Leu Leu Val Asn Thr His Asn Pro Gly Pro Val Arg Tyr Leu Asp Glu
305                 310                 315                 320

Glu Gly Arg Gln Val Ser Thr Ser Ile Arg Arg His Glu Lys Leu Glu
                325                 330                 335

Gly Gln Ser Leu Asp Leu Glu Val Thr Pro Ala Thr Pro Ala Thr Leu
            340                 345                 350

Asp Ile Ala Ser Leu Val Gln Gln Ala Lys Pro Ser Thr Val Lys Ser
            355                 360                 365

Glu Ser Asn Ala Ser Thr Lys Gln Pro Asp Leu Ala Val
            370                 375                 380

<210> SEQ ID NO 3
<211> LENGTH: 1146
<212> TYPE: DNA
<213> ORGANISM: Artificial Sequence
```

<220> FEATURE:
<223> OTHER INFORMATION: Synthetic polynucleotide

<400> SEQUENCE: 3

```
atgctgactt ataaaggcgt tttcaaagcc gctactgttc aggcggaacc ggtgtggatg      60
gacgcagacg cgaccatcac caaagctatc cgtattattg aagaagctgc ggacaacggt     120
gcaaaatttg tagcgtttcc tgaagttttc attccaggtt atccgtggtg gatctggctg     180
ggcaccgcga tgtggggtgc gaagttcgtg gtaccgttcc atgaaaactg tctggaactg     240
ggcgataagc gtatgcagcg cattcaggcc gccgcgaaac aaaatggcat cgcactggta     300
atgggctacg gtaacgcga cggtggtagc cgttacatga ccaggtgtt catcgatgac       360
agcggtaaaa tcgtggcgaa tcgccgtaag ctgaaaccaa ctcacgaaga gcgtaccatt     420
ttcggtgaag gtaacggttc tgatttcatc acgcatgatt tcccttttcgc tcgcgttggt    480
ggttttaatt gctgggaaca cctgcagccg ctgagcaaat acatgatgta tagcctgcaa     540
gaacaggtgc atgtcgcctc ttggccggca atgtgtactt accagccgga cgttccgcag     600
tttggcgcag gtgcgaatga ggcagtgacg cgttcttacg ccatcgaagg tgcgtgctac     660
gttctgggtg ctacgctggt tattggtaag gcggcgcacg atgcattttg cgataccgaa     720
gaacaccaca aactgctggg catgggtggc ggttgggcgc gcatcttcgg tccggacggt     780
gaatatctgg ctgaaagcct ggctcacgac gcagaggta tcctgtacgc cgatattgac      840
ctgtctaaaa tcctgctggc aaaagctaac accgacacgg tcggtcatta tgcacgtccg     900
gatgtcctgt ccctgctggt taacacccac aaccctggtc cggtacgtta cctggacgaa     960
gaaggtcgtc aggtgagcac tagcatccgt cgccacgaaa aactggaggg tcaatctctg    1020
gacctggagg ttactccggc gaccccggcc accctggaca tcgcatctct ggttcagcag    1080
gctaaaccgt ctactgttaa atctgagtcc aacgccagca cgaaacagcc ggacctggcg    1140
gtataa                                                              1146
```

<210> SEQ ID NO 4
<211> LENGTH: 381
<212> TYPE: PRT
<213> ORGANISM: Artificial Sequence
<220> FEATURE:
<223> OTHER INFORMATION: Synthetic polypeptide

<400> SEQUENCE: 4

```
Met Leu Thr Tyr Lys Gly Val Phe Lys Ala Ala Thr Val Gln Ala Glu
1               5                   10                  15

Pro Val Trp Met Asp Ala Asp Ala Thr Ile Thr Lys Ala Ile Arg Ile
            20                  25                  30

Ile Glu Glu Ala Ala Asp Asn Gly Ala Lys Phe Val Ala Phe Pro Glu
        35                  40                  45

Val Phe Ile Pro Gly Tyr Pro Trp Trp Ile Trp Leu Gly Thr Ala Met
    50                  55                  60

Trp Gly Ala Lys Phe Val Val Pro Phe His Glu Asn Cys Leu Glu Leu
65                  70                  75                  80

Gly Asp Lys Arg Met Gln Arg Ile Gln Ala Ala Ala Lys Gln Asn Gly
                85                  90                  95

Ile Ala Leu Val Met Gly Tyr Gly Glu Arg Asp Gly Gly Ser Arg Tyr
            100                 105                 110

Met Ser Gln Val Phe Ile Asp Asp Ser Gly Lys Ile Val Ala Asn Arg
        115                 120                 125
```

-continued

```
Arg Lys Leu Lys Pro Thr His Glu Glu Arg Thr Ile Phe Gly Glu Gly
130                 135                 140

Asn Gly Ser Asp Phe Ile Thr His Asp Phe Pro Phe Ala Arg Val Gly
145                 150                 155                 160

Gly Phe Asn Cys Trp Glu His Leu Gln Pro Leu Ser Lys Tyr Met Met
                165                 170                 175

Tyr Ser Leu Gln Glu Gln Val His Val Ala Ser Trp Pro Ala Met Cys
            180                 185                 190

Thr Tyr Gln Pro Asp Val Pro Gln Phe Gly Ala Gly Ala Asn Glu Ala
        195                 200                 205

Val Thr Arg Ser Tyr Ala Ile Glu Gly Ala Cys Tyr Val Leu Gly Ala
210                 215                 220

Thr Leu Val Ile Gly Lys Ala Ala His Asp Ala Phe Cys Asp Thr Glu
225                 230                 235                 240

Glu His His Lys Leu Leu Gly Met Gly Gly Trp Ala Arg Ile Phe
                245                 250                 255

Gly Pro Asp Gly Glu Tyr Leu Ala Glu Ser Leu Ala His Asp Ala Glu
                260                 265                 270

Gly Ile Leu Tyr Ala Asp Ile Asp Leu Ser Lys Ile Leu Leu Ala Lys
            275                 280                 285

Ala Asn Thr Asp Thr Val Gly His Tyr Ala Arg Pro Asp Val Leu Ser
        290                 295                 300

Leu Leu Val Asn Thr His Asn Pro Gly Pro Val Arg Tyr Leu Asp Glu
305                 310                 315                 320

Glu Gly Arg Gln Val Ser Thr Ser Ile Arg Arg His Glu Lys Leu Glu
                325                 330                 335

Gly Gln Ser Leu Asp Leu Glu Val Thr Pro Ala Thr Pro Ala Thr Leu
            340                 345                 350

Asp Ile Ala Ser Leu Val Gln Gln Ala Lys Pro Ser Thr Val Lys Ser
        355                 360                 365

Glu Ser Asn Ala Ser Thr Lys Gln Pro Asp Leu Ala Val
370                 375                 380

<210> SEQ ID NO 5
<211> LENGTH: 1113
<212> TYPE: DNA
<213> ORGANISM: Artificial Sequence
<220> FEATURE:
<223> OTHER INFORMATION: Synthetic polynucleotide

<400> SEQUENCE: 5
atgctgactt ataaaggcgt tttcaaagcc gctactgttc aggcggaacc ggtgtggatg      60
gacgcagacg cgaccatcac caaagctatc cgtattattg aagaagctgc ggacaacggt     120
gcaaaatttg tagcgtttcc tgaagttttc attccaggtt atccgtggtg gatctggctg     180
ggcaccgcga tgtggggtgc gaagttcgtg gtaccgttcc atgaaaaactg tctggaactg     240 ggcgataagc gtatgcagcg cattcaggcc gccgcgaaac aaaatggcat cgcactggta     300
atgggctacg gtgaacgcga cggtggtagc cgttacatga gccaggtgtt catcgatgac     360
agcggtaaaa tcgtggcgaa tcgccgtaag ctgaaaccaa ctcacgaaga gcgtaccatt     420
ttcggtgaag gtaacggttc tgatttcatc acgcatgatt tcccctttcgc tcgcgttggt     480 ggtttttaatt gctgggaaca cctgcagccg ctgagcaaat acatgatgta tagcctgcaa     540
gaacaggtgc atgtcgcctc ttggccggca atgtgtactt accagccgga cgttccgcag     600
ctgggcgcag gtgcgaatga ggcagtgacg cgttcttacg ccatcgaagg tgcgtgctac     660
```

```
gttctgggtg ctacgctggt tattggtaag gcggcgcacg atgcattttg cgataccgaa    720
gaacaccaca aactgctggg catgggtggc ggttgggcgc gcatcttcgg tccggacggt    780
gaatatctgg ctgaaagcct ggctcacgac gcagagggta tcctgtacgc cgatattgac    840
ctgtctaaaa tcctgctggc aaaagctaac accgacacgg tcggtcatta tgcacgtccg    900
gatgtcctgt ccctgctggt aacacccac aaccctggtc cggtacgtta cctggacgaa    960
gaaggtcgtc tggatgttaa cacgcgttcc cgtgtagaaa actttcgcct gcgtcaggca   1020
gcagaacagg aacgtcaggc cagcaaacgt ctgggcacga aactgtttga acagtctctg   1080
ctggcggagg agccggtacc agccaaactc gag                                1113
```

<210> SEQ ID NO 6
<211> LENGTH: 371
<212> TYPE: PRT
<213> ORGANISM: Artificial Sequence
<220> FEATURE:
<223> OTHER INFORMATION: Synthetic polypeptide

<400> SEQUENCE: 6

```
Met Leu Thr Tyr Lys Gly Val Phe Lys Ala Ala Thr Val Gln Ala Glu
1               5                   10                  15

Pro Val Trp Met Asp Ala Asp Ala Thr Ile Thr Lys Ala Ile Arg Ile
            20                  25                  30

Ile Glu Glu Ala Ala Asp Asn Gly Ala Lys Phe Val Ala Phe Pro Glu
        35                  40                  45

Val Phe Ile Pro Gly Tyr Pro Trp Trp Ile Trp Leu Gly Thr Ala Met
    50                  55                  60

Trp Gly Ala Lys Phe Val Val Pro Phe His Glu Asn Cys Leu Glu Leu
65                  70                  75                  80

Gly Asp Lys Arg Met Gln Arg Ile Gln Ala Ala Lys Gln Asn Gly
                85                  90                  95

Ile Ala Leu Val Met Gly Tyr Gly Glu Arg Asp Gly Ser Arg Tyr
            100                 105                 110

Met Ser Gln Val Phe Ile Asp Asp Ser Gly Lys Ile Val Ala Asn Arg
        115                 120                 125

Arg Lys Leu Lys Pro Thr His Glu Glu Arg Thr Ile Phe Gly Glu Gly
    130                 135                 140

Asn Gly Ser Asp Phe Ile Thr His Asp Phe Pro Phe Ala Arg Val Gly
145                 150                 155                 160

Gly Phe Asn Cys Trp Glu His Leu Gln Pro Leu Ser Lys Tyr Met Met
                165                 170                 175

Tyr Ser Leu Gln Glu Gln Val His Val Ala Ser Trp Pro Ala Met Cys
            180                 185                 190

Thr Tyr Gln Pro Asp Val Pro Gln Leu Gly Ala Gly Ala Asn Glu Ala
        195                 200                 205

Val Thr Arg Ser Tyr Ala Ile Glu Gly Ala Cys Tyr Val Leu Gly Ala
    210                 215                 220

Thr Leu Val Ile Gly Lys Ala Ala His Asp Ala Phe Cys Asp Thr Glu
225                 230                 235                 240

Glu His His Lys Leu Leu Gly Met Gly Gly Trp Ala Arg Ile Phe
                245                 250                 255

Gly Pro Asp Gly Glu Tyr Leu Ala Glu Ser Leu Ala His Asp Ala Glu
            260                 265                 270

Gly Ile Leu Tyr Ala Asp Ile Asp Leu Ser Lys Ile Leu Leu Ala Lys
```

```
              275                 280                 285
Ala Asn Thr Asp Thr Val Gly His Tyr Ala Arg Pro Asp Val Leu Ser
    290                 295                 300

Leu Leu Val Asn Thr His Asn Pro Gly Pro Val Arg Tyr Leu Asp Glu
305                 310                 315                 320

Glu Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
                355                 360                 365

Lys Leu Glu
    370

<210> SEQ ID NO 7
<211> LENGTH: 141
<212> TYPE: DNA
<213> ORGANISM: Acidovorax facilis

<400> SEQUENCE: 7
ctggatgtta acacgcgttc ccgtgtagaa aactttcgcc tgcgtcaggc agcagaacag      60
gaacgtcagg ccagcaaacg tctgggcacg aaactgtttg aacagtctct gctggcggag     120
gagccggtac agccaaaata g                                               141

<210> SEQ ID NO 8
<211> LENGTH: 48
<212> TYPE: PRT
<213> ORGANISM: Acidovorax facilis

<400> SEQUENCE: 8

Leu Asp Val Asn Thr Arg Ser Arg Val Glu Asn Phe Arg Leu Arg Gln
1               5                   10                  15

Ala Ala Glu Gln Glu Arg Gln Ala Ser Lys Arg Leu Gly Thr Lys Leu
            20                  25                  30

Phe Glu Gln Ser Leu Leu Ala Glu Glu Pro Val Pro Ala Lys Leu Glu
        35                  40                  45

<210> SEQ ID NO 9
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 9
ccggacgttc cgcagtttgg cgcaggtgcg aatg                                  34

<210> SEQ ID NO 10
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 10
cattcgcacc tgcgccaaac tgcggaacgt ccgg                                  34

<210> SEQ ID NO 11
<211> LENGTH: 41
<212> TYPE: DNA
```

```
<213> ORGANISM: Artificial sequence
<220> FEATURE:
<223> OTHER INFORMATION: Synthetic polynucleotide

<400> SEQUENCE: 11
acctggacga agaaggtcgt ctggatgtta acacgcgttc c                    41

<210> SEQ ID NO 12
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 12
ttgttagcag ccggatctca gtggtggtgg tggtggtgc                       39

<210> SEQ ID NO 13
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 13
tgagatccgg ctgctaacaa a                                          21

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 14
acgaccttct tcgtccaggt aa                                         22
```